(12) United States Patent
Knauf et al.

(10) Patent No.: US 8,729,309 B2
(45) Date of Patent: May 20, 2014

(54) METHOD FOR PRODUCING NITROBENZENE BY ADIABATIC NITRIDING

(75) Inventors: Thomas Knauf, Dormagen (DE); Alexandre Racoes, Krefeld (DE); Andreas Karl Rausch, Kaarst (DE); Dietrich Wulf, Köln (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/812,653

(22) PCT Filed: Jul. 26, 2011

(86) PCT No.: PCT/EP2011/062827
§ 371 (c)(1),
(2), (4) Date: Apr. 8, 2013

(87) PCT Pub. No.: WO2012/013672
PCT Pub. Date: Feb. 2, 2012

(65) Prior Publication Data
US 2013/0197268 A1    Aug. 1, 2013

(30) Foreign Application Priority Data
Jul. 28, 2010   (DE) .......................... 10 2010 038 519

(51) Int. Cl.
*C07B 43/02*  (2006.01)
*C07C 201/00*  (2006.01)
*C07C 209/00*  (2006.01)

(52) U.S. Cl.
USPC .......................................... 564/419; 564/411

(58) Field of Classification Search
None
See application file for complete search history.

(56) References Cited

U.S. PATENT DOCUMENTS

| | | |
|---|---|---|
| 2,256,999 A | 9/1941 | Castner |
| 3,928,475 A | 12/1975 | Dassel |
| 3,981,935 A | 9/1976 | McCall |
| 4,091,042 A | 5/1978 | Alexanderson et al. |
| 5,313,009 A | 5/1994 | Guenkel et al. |
| 5,763,697 A | 6/1998 | Hermann et al. |
| 5,808,157 A | 9/1998 | Langer et al. |
| 2007/0249873 A1 | 10/2007 | Knauf et al. |
| 2008/0234518 A1 | 9/2008 | Sommer et al. |
| 2009/0187051 A1 | 7/2009 | Rausch et al. |
| 2010/0076230 A1 | 3/2010 | Knauf et al. |

FOREIGN PATENT DOCUMENTS

| | | |
|---|---|---|
| CA | 1260958 A1 | 9/1989 |
| DE | 102008048713 A1 | 3/2010 |
| DE | 102009005324 A1 | 7/2010 |
| EP | 0696573 A1 | 2/1996 |
| EP | 1816117 A1 | 8/2007 |
| EP | 1882681 A1 | 1/2008 |
| EP | 2070907 A1 | 6/2009 |

OTHER PUBLICATIONS

International Search Report for PCT/EP2011/062827 mailed Feb. 17, 2012.
Search Report and First Office Action, issued in Chinese Application No. 201180036942.X on Dec. 3, 2013.

*Primary Examiner* — Clinton Brooks
(74) *Attorney, Agent, or Firm* — Novak Druce Connolly Bove + Quigg LLP

(57) ABSTRACT

The invention relates to a process for the continuous production of nitrobenzene by nitration of benzene with a mixture of nitric acid and sulfuric acid under adiabatic conditions, in which unreacted benzene is separated from the crude product obtained after phase separation before washing thereof, using the adiabatic heat of reaction.

9 Claims, 1 Drawing Sheet

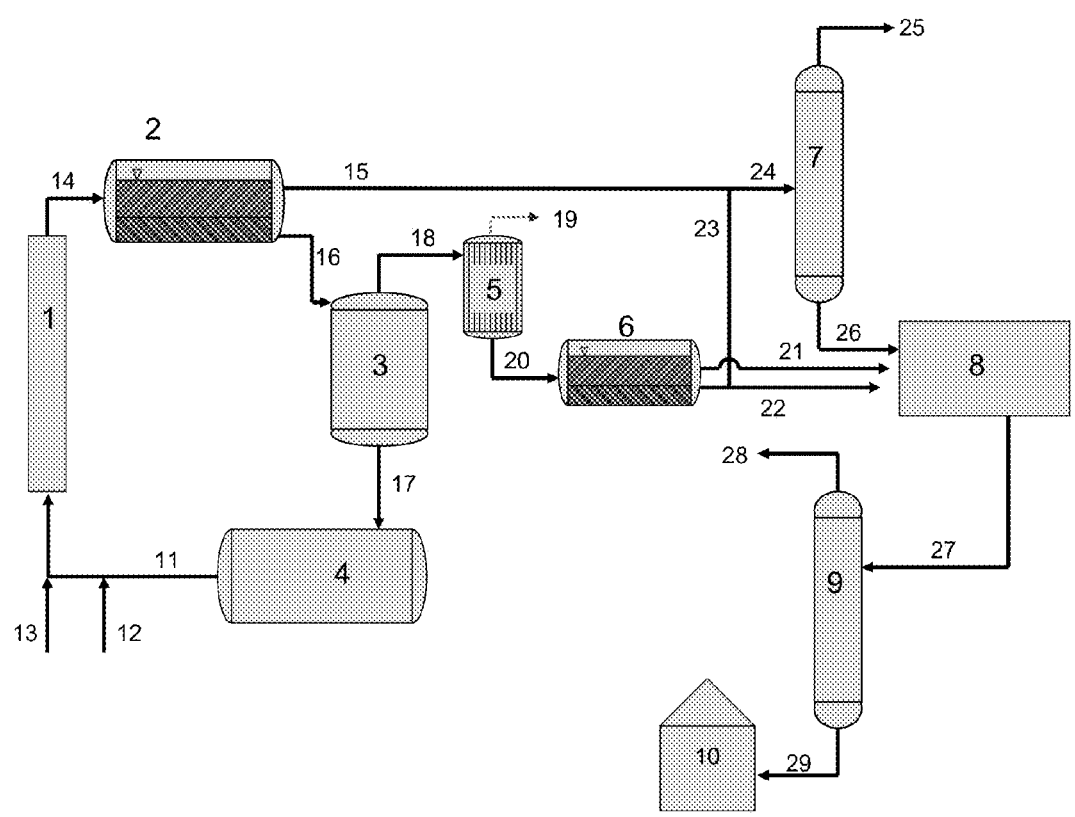

METHOD FOR PRODUCING NITROBENZENE BY ADIABATIC NITRIDING

RELATED APPLICATIONS

This application is a national stage application (under 35 U.S.C. §371) of PCT/EP2011/062827, filed Jul. 26, 2011, which claims benefit of German Patent Application No. 10 2010 038 519.0, filed Jul. 28, 2010.

The invention relates to a process for the continuous production of nitrobenzene by nitration of benzene with a mixture of nitric acid and sulfuric acid under adiabatic conditions, in which unreacted benzene is separated from the crude product obtained after phase separation before washing thereof, using the adiabatic heat of reaction.

The nitration of benzene with nitric acid to give a crude nitrobenzene has already been the subject of many publications and patent applications. A continuous process for the production of nitrobenzene by adiabatic nitration of benzene by means of a mixture of sulfuric acid and nitric acid (so-called mixed acid) was claimed for the first time in U.S. Pat. No. 2,256,999 and is described in current forms in U.S. Pat. No. 4,091,042, U.S. Pat. No. 5,313,009 and U.S. Pat. No. 5,763,697.

It is a common feature of the described adiabatic processes that the starting materials benzene and nitric acid are reacted in a large excess of sulfuric acid, which takes up the heat of reaction that is liberated and the water that is formed during the reaction. It is a feature of the adiabatic processes cited above that part of the heat of reaction stored in the reaction mixture is used to re-concentrate the sulfuric acid which has been diluted by the water of reaction formed and by the water introduced with the nitric acid. The remaining heat of reaction remains in the organic phase of the reaction mixture.

U.S. Pat. No. 5,313,009 describes a process for the adiabatic production of nitrobenzene in which nitric acid and sulfuric acid are mixed to form the so-called mixed acid and benzene is metered into the mixed acid and reacts with the nitric acid to form water and substantially nitrobenzene. The temperature of the reaction mixture and the concentrations of benzene, nitric acid and sulfuric acid are so chosen that a substantially nitric-acid-free mixture of benzene, nitrobenzene, sulfuric acid and water is obtained downstream of a reaction zone. Benzene is used at least in stoichiometric amounts, based on the amount of nitric acid.

The substantially nitric-acid-free reaction mixture obtained downstream of the reaction zone is fed to a phase separator in which two phases form, an organic phase and an aqueous phase. The organic phase is referred to as crude nitrobenzene and consists substantially of nitrobenzene, benzene, and a certain amount of sulfuric acid and water dissolved in the nitrobenzene. The aqueous phase is referred to as spent acid and consists substantially of water, sulfuric acid, and nitrobenzene dissolved in the sulfuric acid.

The spent acid separated off in the phase separator is introduced into an apparatus for flash evaporation of the water, in which water is evaporated from the spent acid by means of a sudden pressure drop and using the high temperature of the spent acid, which was achieved as a result of the adiabatic reaction procedure, so that concentrated sulfuric acid is obtained, the concentration of which corresponds substantially to the concentration upstream of the reaction zone. A use of the heat of reaction other than for concentrating the sulfuric acid is not described in U.S. Pat. No. 5,313,009. This process is therefore disadvantageous because the heat of reaction that is liberated is not used completely.

U.S. Pat. No. 4,091,042 (column 3, lines 44-58) describes a process for the production of nitrobenzene in which the reaction is carried out in four series-connected stirred vessels, the reaction mixture leaving the fourth stirred vessel being passed into a continuously operated phase separator in which the spent acid is separated from the organic phase. The spent acid is concentrated in a flash evaporator under reduced pressure using the heat of reaction stored in the spent acid. The organic phase is introduced continuously into a four-stage counter-current extraction washer, where acidic constituents such as sulfuric acid residues, dinitrophenol and picric acid are extracted by contact with sodium carbonate solution. The washed organic phase is subjected to steam distillation in order to recover the excess benzene. The amount of excess benzene in the product can be from 0.28% to 10.4% in this process (see table for Examples 4 to 9), the excess benzene resulting from the conversion of the reaction and no technical measures being taken in this process to reduce the benzene content in the crude nitrobenzene. This process too is disadvantageous because not all the heat of reaction that is liberated is used, only the portion that is stored in the spent acid.

U.S. Pat. No. 5,763,697 (column 6, lines 17-28) describes a process for the production of nitrobenzene in which the nitration mixture leaving the tubular reactor is separated in a static or dynamic phase separator. The spent acid obtained is fed to purification and concentration. The nitrobenzene that is separated off, containing about 5% to 10% benzene, is fed to a washing step for the purpose of removing traces of dissolved nitric acid, nitrous gases and nitrophenols and is then freed of residual benzene and water in a drying or distillation step. The energy stored in the organic phase is not used, nor is there a technical measure for reducing the benzene content in the nitrobenzene prior to washing.

However, there have also been attempts to separate excess benzene from the reaction mixture with the aid of the heat of reaction.

U.S. Pat. No. 3,928,475 describes a process for the production of nitrobenzene in which benzene and nitric acid in approximately stoichiometric proportions are introduced into a reaction vessel containing nitrobenzene, benzene and sulfuric acid and mixed therein, and a water/benzene azeotropic mixture is evaporated from this mixture, the aqueous phase of the azeotropic mixture containing nitric acid and the organic phase of the azeotropic mixture also containing nitrobenzene in addition to benzene. This process is disadvantageous, however, because the heat of reaction must also be used to evaporate nitric acid and nitrobenzene. In addition, the dilute nitric acid contained in the aqueous phase of the azeotropic mixture cannot be fed back into the reaction vessel but is disposed of for waste water treatment.

U.S. Pat. No. 3,981,935 represents a form of the process described in U.S. Pat. No. 3,928,475 which is disadvantageous in the same manner. In this form of the process, the organic phase of the azeotropic mixture is reacted further in a post-reactor and is not fed back into the main reactor. The disadvantages of U.S. Pat. No. 3,928,475 therefore persist unchanged.

The process concept of producing nitrobenzene with simultaneous azeotropic distillation is also described by Hochstrasser and Renken (P. Hochstrasser, A. Renken, Chem.-Ing. Tech. 59 (1987), No. 2, p. 172-173), the problem of nitric acid losses being discussed in detail therein. Accordingly, when the reaction and the distillation are carried out simultaneously, a comparatively high nitric acid loss is always to be expected because nitric acid is discharged with the evaporated water of reaction and a further source of loss is thus added to the losses which in any case occur as a result of a certain solubility of nitric acid in the organic phase.

According to the prior art, the crude nitrobenzene formed in the reaction apparatuses and separated from the acid phase is subjected to washing and working up by distillation, as described, for example, in EP 1 816 117 A1 (page 2, lines 26-42), U.S. Pat. No. 4,091,042 (see above) or U.S. Pat. No. 5,763,697 (see above). This procedure means cooling of crude nitrobenzene from the reaction end temperature, which is conventionally from 100° C. to 145° C., to less than 50° C. for the washing step. Separation by distillation, which serves to separate off excess benzene, requires the entire product stream to be reheated to the boiling temperature of nitrobenzene, that is to say 211° C. at atmospheric pressure or correspondingly lower at reduced pressure, for example 170° C. at 350 hPa. This process is disadvantageous because the energy content of the crude nitrobenzene stream is not used completely since the temperature level is low, and in addition the crude nitrobenzene stream must be heated after washing using additionally purchased energy. Because of the required re-heating after washing, this process is disadvantageous from the point of view of energy but is also complex in terms of apparatus because the distillation column at the end of the process must be so equipped that the nitrobenzene stream cooled for the washing with water can be heated to the boiling point again.

Accordingly, it was an object of the present invention to provide a process which reduces the energy outlay of nitrobenzene production by optimising the use of the heat of reaction and at the same time allows advantages to be achieved in terms of apparatus.

Surprisingly, it has been found that the object can be achieved by a process for the continuous production of nitrobenzene by a) nitration of benzene with a mixture of nitric acid and sulfuric acid (mixed acid) under adiabatic conditions;

b) separation of the process product obtained in step a) by phase separation into an aqueous phase, which contains at least sulfuric acid, nitrobenzene and benzene (=spent acid), and an organic phase, which contains at least nitrobenzene and benzene (=crude nitrobenzene);

c) transfer of the aqueous phase obtained in step b) into an evaporator in which the sulfuric acid is concentrated by pressure reduction, wherein a gaseous stream containing at least water, nitrobenzene and benzene is removed from the evaporator and then condensed, and wherein the resulting concentrated sulfuric acid is fed back into step a);

d) separation by distillation of from 20% by mass to 100% by mass, preferably from 50% by mass to 100% by mass, particularly preferably from 90% by mass to 100% by mass, of the benzene contained in the organic phase obtained in step b) by evaporation of benzene using the adiabatic heat of reaction obtained in step a) in the evaporation, wherein a pre-purified nitrobenzene depleted of benzene is obtained;

e) washing of the pre-purified nitrobenzene obtained in step d) and subsequent separation of water by phase separation, wherein purified nitrobenzene is obtained.

Under adiabatic conditions means that the reaction between benzene and mixed acid (step a)) is not thermostatically regulated. The starting materials benzene and mixed acid are each brought to the desired temperature, mixed and then react with one another without the (considerable) heat of reaction being dissipated by a cooling medium. In this procedure, the heat of reaction is reflected quantitatively (with the exception of slight, unavoidable heat losses) in the temperature rise of the reaction mixture.

If the separation of the benzene by distillation is carried out, as proposed according to the invention, before the washing step, the following advantages are obtained:

i) The heat of reaction stored in the crude nitrobenzene can be used for the evaporation of the benzene in step d). Accordingly, heating, as is required in the distillation that is conventional in the prior art after the washing step, is no longer required, resulting in a considerable energy saving (Example 2).

ii) It is possible to dispense with the distillation column and the heat exchanger that are conventional in the prior art downstream of the washing step, provided that it is ensured that the nitrobenzene can be fed to its further use even if it is saturated with water. This is the case, for example, when the nitrobenzene is used in a process for aniline production because water forms in any case during the synthesis of aniline and therefore does not interfere with the process and can even be advantageous (see EP 0 696 573 B1 and EP 1 882 681 A1).

iii) The alternative benzene separation in step d) additionally has the advantage that the separation of benzene immediately after reaction (step a)) and phase separation (step b)) also reduces the hydraulic load in the washing step (step e)).

iv) As a result of the benzene separation before the washing step, the phase separation times in the washing step (step e)) are shortened, so that the volumes of the containers provided for the phase separation can be reduced (see Example 5).

By using the heat of reaction stored in the organic phase, the process for the production of nitrobenzene is therefore optimised not only in terms of energy but also in terms of apparatus.

The process according to the invention is characterised by a number of features which are not found in the prior art. For example, in the production of nitrobenzene according to the invention by adiabatic nitration of benzene with subsequent separation of benzene from the reaction mixture even before the washing step, higher plant availability, lower maintenance costs, lower investment costs and lower energy costs are achieved as compared with the processes conventional hitherto, in which the separation of benzene does not take place until the last step of the nitrobenzene working up. In addition to the surprisingly positive energy- and apparatus-related effects, the procedure according to the invention is also not obvious to the person skilled in the art because high material-related demands must be made in terms of the handling of the crude nitrobenzene owing to its acid content, resulting in additional costs. According to the prior art, the person skilled in the art would not separate off the benzene before the washing step owing to the material-related problems, because he would have to use an acid-resistant and accordingly comparatively expensive material, without being aware, on the basis of his general specialist knowledge, that these additional costs pay for themselves again at other points in the process.

Steps a) and b) of the process according to the invention can be carried out according to any desired process for the production of nitrobenzene, provided that the process in step a) is an adiabatic process and the temperature of the crude nitrobenzene obtained in step b) is from >100° C. to 145° C., preferably from >120° C. to 140° C. Preferably, step a) of the process according to the invention is carried out as described in DE 10 2008 048713 A1, paragraph [0024], which is accordingly considered to be part of the present disclosure.

Steps b) and c) of the process according to the invention are known in principle from the prior art. Preferably, steps b) and c) are carried out as described in EP 2 070 907 A1, paragraphs [0024] and [0027], which is accordingly considered to be part of the present disclosure.

In step d), the benzene is separated partially to completely from the crude nitrobenzene in a thermal separation operation, which is preferably in the form of a distillation column with a plurality of theoretical plates. The procedure is preferably carried out at reduced pressure, preferably at absolute pressures at the head of the distillation column of from 0.05 bar to 1.0 bar, particularly preferably from 0.1 bar to 0.5 bar. As well as containing the crude nitrobenzene stream from step b), the feed to the distillation column can also include the organic stream which is obtained in the sulfuric acid concentration in step c) by condensation of the gaseous stream containing at least water, nitrobenzene and benzene and subsequent separation of the water from the condensate in a phase separator. Accordingly, in this specific embodiment, the invention provides a process in which the condensed gaseous stream obtained in step c), containing at least water, nitrobenzene and benzene, is fed, after separation of water, to the separation by distillation of benzene in step d).

The feed to the distillation column preferably contains from 2.0% by mass to 15% by mass benzene, based on the total mass of the feed. The by-products of the benzene nitration (in particular dinitrobenzene and nitrophenols) as well as water and sulfuric acid are additionally present in the feed to the distillation column. Nitric acid as well as dissolved nitrous gases can also be present.

The distillation column can be of any desired configuration, preferably in the form of a packed or plate column. The distillation column should have from 3 to 40, preferably from 5 to 20, particularly preferably from 7 to 15, theoretical plates. The distillation column can be configured with or without heating. If complete separation of the benzene is desired, additional heating is preferred, for example by means of a circulation evaporator, because complete benzene separation generally requires more energy than is stored in the crude nitrobenzene in an adiabatic reaction procedure. Owing to the presence of dissolved nitrous gases, it can be expedient to feed an inert gas into the distillation column in order to allow the gaseous nitric oxides to be discharged effectively.

The benzene that is separated off is liquefied by single- or multi-stage condensation and fed to a phase separator in order to separate off water that has likewise condensed. The separated benzene is preferably fed back into the reaction (step a)). To that end, it should contain less than 10% by mass nitrobenzene, preferably less than 4.0% by mass nitrobenzene, in each case based on the total mass of the benzene-containing stream to be fed back into the reaction (step a)), particularly preferably no nitrobenzene at all.

If the crude nitrobenzene obtained in step b) is to be freed of benzene as completely as possible, the distillation in step d) is so configured (for example by means of a correspondingly high number of theoretical plates) that the desired residual benzene contents are achieved. This embodiment of the invention in particular provides a process in which in step d) from >99.80% by mass to 100% by mass, preferably from >99.95% by mass to 99.99% by mass, particularly preferably from >99.99% by mass to 99.999% by mass, of the benzene contained in the organic phase obtained in step b) are separated off by distillation. 100% separation of the benzene can be technically very complex, so that in preferred embodiments a small residual amount (preferably 100 ppm, particularly preferably 10 ppm) of the benzene is not separated off.

In many cases, the purified nitrobenzene obtained in step e) can be used further without further purification or drying steps. Accordingly, this embodiment of the invention provides a process in which the purified nitrobenzene obtained in step e) is not purified further and is fed directly to further uses. Preference is given to the use of a purified nitrobenzene obtained by the process according to the invention according to steps a) to e) in hydrogenation to aniline.

It is also possible to separate off benzene only partially in step d). This embodiment of the invention provides a process in which in step d) from 20% by mass to 99.8% by mass, preferably from 50% by mass to 95% by mass, particularly preferably from 70% by mass to 85% by mass, of the benzene contained in the organic phase obtained in step b) are separated off. This procedure is also advantageous in that a partial separation of the benzene reduces the phase separation time in the washing step. In a preferred form of the only partial separation of the benzene before the washing step, this is followed by separation by distillation of the residual benzene and of the water present from the purified nitrobenzene. Accordingly, this preferred embodiment of the invention provides a process in which in step d) from 20% by mass to 99.8% by mass, preferably from 50% by mass to 95% by mass, particularly preferably from 70% by mass to 85% by mass, of the benzene contained in the organic phase obtained in step b) are separated off and step e) is followed by:

f) separation by distillation of benzene and water from the purified nitrobenzene obtained in step e), wherein dried pure nitrobenzene is obtained.

Whether it is advantageous to carry out the process according to the invention according to steps a) to e) or according to steps a) to f) depends on the one hand on the intended use of the nitrobenzene. Uses for which dry nitrobenzene is essential require the process according to the invention to be carried out according to steps a) to f), while both embodiments can in principle be used in the case of uses of nitrobenzene in which water is not disruptive. Which embodiment is advantageous in the latter case then depends mostly on the given boundary conditions of a production plant. If, for example, a nitrobenzene plant is being newly built, it can be advantageous to omit step f) because a distillation apparatus can thereby be saved. If the process according to the invention is to be integrated into an existing production plant which already has a distillation apparatus suitable for step f), then the embodiment according to steps a) to f) may be more expedient. It is therefore wholly conceivable that, for the same intended uses of the nitrobenzene and accordingly the same purity criteria, the embodiment consisting of steps a) to e) is advantageous in one case and the embodiment consisting of steps a) to f) is advantageous in another.

If it is advantageous to carry out the process according to the invention according to steps a) to f), then it is generally not necessary for step f) to be followed by further purification steps (such as distillation of the nitrobenzene itself). Accordingly, this embodiment of the invention provides a process in which the dried pure nitrobenzene obtained in step f) is not purified further and is fed directly to further uses. Preference is given to the use of a dried pure nitrobenzene obtained by the process according to the invention according to steps a) to f) in hydrogenation to aniline.

A preferred embodiment of the process is shown in FIG. 1. A sulfuric acid stream (11), a nitric acid stream (12) and a benzene stream (13) are fed to a reactor (1). When the nitric acid has reacted completely with the benzene in an adiabatic reaction procedure to give nitrobenzene, the reaction product (14), which is then at a temperature of about 130° C., is fed to a phase separator (2) in which the reaction product (14)

decomposes into an organic phase ((15)=crude nitrobenzene, containing benzene in addition to nitrobenzene) and an aqueous phase ((16)=spent acid, containing small amounts of nitrobenzene and benzene in addition to sulfuric acid). The aqueous phase (16) containing mainly sulfuric acid is subjected to flash evaporation of water in an evaporator (3) by sudden pressure reduction (to from 60 mbar to 120 mbar; (19)=in the direction of the vacuum pump) and thus concentrated. The concentrated sulfuric acid (17) is stored in the sulfuric acid tank (4) for further use. In the concentration of the sulfuric acid there is obtained a vapour stream (18) containing water, sulfuric acid, nitrobenzene and benzene, and this vapour stream (18) is condensed in a condenser (5). The liquefied condensate (20) is separated into an organic phase and an aqueous phase in a phase separator (6), and the aqueous phase (21) is fed to washing while the organic phase is either likewise fed to washing (22) or—preferably—is combined with the crude nitrobenzene (15) via (23) to form stream (24). Stream (24)—consisting of the crude nitrobenzene from the phase separator (15) and optionally from stream (23)—is fed to an apparatus for benzene separation (7), in which benzene and water are separated off at the head (25) and a pre-purified nitrobenzene depleted of benzene is obtained as the bottom product (26), which has been freed wholly or partially of benzene. The pre-purified nitrobenzene (26) is fed to washing (8). The resulting stream of purified nitrobenzene (27) largely freed of nitrophenols and salts can optionally be heated again and freed in a distillation column (9) of water and any benzene still present, both of which are separated off at the head (28), as a result of which dried pure nitrobenzene (29) is obtained and stored in tank (10).

Washing of the pre-purified nitrobenzene is preferably carried out in the form of an at least three-stage extraction, which is preferably performed as a counter-current extraction. Washing is preferably carried out in a temperature range from 20° C. to 95° C.

In the first stage excess sulfuric acid is separated off by contact with water (so-called acid washing), in the second stage organic by-products are extracted by contact with an alkaline wash water (so-called alkaline washing) and finally in the third stage (so-called neutral washing) excess lye and salts are separated off. Accordingly, this embodiment of the invention provides a process in which the washing in step e) consists of at least one of each of an acid, alkaline and neutral washing stage.

It is possible to omit the acid washing, but the requirement for lye in the alkaline washing increases as a result. Suitable lyes are ammonia water, alkali carbonates and hydrogen carbonates, as well as alkali and alkaline earth hydroxides.

Neutral washing can be performed as a single-stage or multi-stage washing with water. Neutral washing can also be replaced by using membrane modules or centrifuges to separate off the lye residues and salts. Neutral washing can also be omitted completely if a nitrobenzene quality that satisfies customer requirements has already been obtained beforehand. For example, the concentrations of nitrophenols at the end of the washing are to be less than 200 ppm, preferably less than 20 ppm, particularly preferably less than 5 ppm.

EXAMPLES

Examples 1 to 4 below are based on Aspen simulations, which were validated on an existing nitrobenzene plant. The basic procedure is shown in FIG. 1, but not all the apparatuses were used, depending on the example.

Example 1 (Comparison Example)

Separation by Distillation of the Benzene after Washing

In this example, the process was simulated without apparatus (7). Therefore, streams (15), (21) and (22) pass directly to washing (8). Stream (27) must be heated from 40° C. to 170° C. in order to separate off benzene at 350 mbar to a content of 100 ppm in column (9). The energy requirement for complete separation of the benzene in column (9) corresponds to that required to heat the stream (27) and is 39.2 kW/$t_{nitrobenzene}$.

Example 2 (According to the Invention)

Partial Separation by Distillation of the Benzene Only from Stream (15) Before Washing In this example, the process was simulated with apparatus (7) as a distillation column with 7 theoretical plates and an evaporator. The feed (24) consists only of the crude nitrobenzene stream (15) at a temperature of 127° C., which contains 7% by mass benzene. Streams (21) and (22) accordingly go directly to washing (8). Column (7) is operated at 350 mbar in such a manner that the benzene content in stream (26) is only 2% by mass benzene. 15.5 kW/$t_{nitrobenzene}$ are required therefor. However, because stream (26) has an outlet temperature of 146° C., 7.5 kW/$t_{nitrobenzene}$ can be recovered by energy integration to produce 1.5 bar steam. Because part of the benzene has already been separated off, column (9) has to be operated only with an energy supply of 29.4 kW/$t_{nitrobenzene}$ in order to reduce the benzene content to 100 ppm. Accordingly, the total energy requirement for separating off the benzene in columns (7) and (9), taking into account the energy integration at column (7), is only 37.4 kW/$t_{nitrobenzene}$.

Example 3 (According to the Invention)

Partial Separation by Distillation of the Benzene from the Combined Streams (15) and (23) Before Washing In this example, the process was simulated with apparatus (7) as a distillation column with 6 theoretical plates and an evaporator. The feed (24) consists on the one hand of the crude nitrobenzene stream (15) at a temperature of 127° C., which contains 7% by mass benzene, and on the other hand of the condensate stream (23) at a temperature of 40° C., which likewise contains 7% by mass benzene. A mixed temperature of 110° C. is obtained for the column feed (24). The column (7) is operated at 150 mbar in such a manner that the benzene content in stream (26) is only 2% by mass benzene. 13.2 kW/$t_{nitrobenzene}$ are required therefor. Because stream (26) has an outlet temperature of only 115° C., owing to the low pressure of 150 mbar, no energy integration is taken into account for this case. Because part of the benzene has already been separated off, column (9) has to be operated only with an energy supply of 23.6 kW/$t_{nitrobenzene}$ in order to reduce the benzene content to 100 ppm. Accordingly, the total energy requirement for separating off the benzene in columns (7) and (9) is only 36.8 kW/$t_{nitrobenzene}$.

Example 4 (According to the Invention)

Complete Separation by Distillation of the Benzene from the Combined Streams (15) and (23) Before Washing In this example, the process was simulated with apparatus (7) as a distillation column with 10 theoretical plates and an evaporator. The feed (24) consists on the one hand of the crude nitrobenzene stream (15) at a temperature of 127° C., which contains 7% by mass benzene, and on the other hand of condensate stream (23) at a temperature of 40° C., which likewise contains 7% by mass benzene. A mixed temperature of 115° C. is obtained for the column feed (24). The column (7) is operated at 350 mbar in such a manner that the benzene content in stream (26) is only 100 ppm. A heating power of 41.2 kW/$t_{nitrobenzene}$ is required therefor at the evaporator of column (7). However, because stream (26) has an outlet temperature of 170° C., 22.3 kW/$t_{nitrobenzene}$ can be recovered by energy integration to produce 1.5 bar steam. Because the benzene has already been removed completely from the nitrobenzene, distillation after washing is dispensed with and column (9) is omitted completely. Accordingly, the total energy requirement for separating off the benzene in column (7), taking into account the energy integration, is only 18.9 kW/$t_{nitrobenzene}$.

TABLE 1

Key data of Examples 1 to 4

| Example: | 1 | 2 | 3 | 4 |
|---|---|---|---|---|
| Form of benzene separation | Complete separation after washing (conventional) | Partial separation before washing without stream (23) | Partial separation before washing with stream (23) | Complete separation before washing with stream (23) |
| Number of plates in column (7) | n.a. | 7 | 6 | 10 |
| Pressure level in column (7) (mbar) | n.a. | 350 | 150 | 350 |
| Pressure level in column (9) (mbar) | 350 | 350 | 350 | n.a. |
| Benzene content in column feed (24) (% by mass) | n.a. | 7 | 7 | 7 |
| Benzene content in column discharge (26) (% by mass) | 7 | 2 | 2 | 0.01 |
| Residual benzene in the pure nitrobenzene (29) (ppm) | 100 | 100 | 100 | 100 |
| Specific energy requirement (KW/$t_{nitrobenzene}$) | 39.2 | 37.4 | 36.8 | 18.9 | n.a.: not applicable because the apparatus was not part of the simulation

TABLE 2

Results of Example 5

| (a) Tests relating to acid washing with crude nitrobenzene containing 2000 ppm nitrophenols | | | |
|---|---|---|---|
| Benzene content | 2% | 6% | 9% |
| Phase separation time | 78 s | 212 s | 238 s |
| (b) Tests relating to neutral washing with purified nitrobenzene | | | |
| Benzene content | 0% | 4% | 9% |
| Phase separation time | 11 s | 18 s | 31 s |

Example 5 (to Illustrate the Relationship Between Phase Separation and Benzene Content)

In order to investigate the influence of the benzene content on the phase separation, nitrobenzene having benzene contents of from 0% by mass to 9% by mass, in each case based on the total mass of the mixture, was used. The nitrobenzene in case a) contained 2000 ppm of nitrophenols and residues of sulfuric acid and in case b) was free of nitrophenols and acid. Therefore, the case of acid washing was reproduced in samples (a), and neutral washing in case b). For both cases, the benzene content was varied in order to check whether previous benzene separation is noticeable in the washing. In a 2-liter stirred container, in each case 1 liter of the nitrobenzene sample was stirred with in each case 360 ml of distilled water for one minute at 500 rpm using a disk stirrer. After stopping the stirrer, the time to complete phase separation was determined (see Table 2). The example shows that a low benzene content both in the acid washing and in the neutral washing has a positive effect on the phase separation time, and a reduction in the container size required for the phase separation can accordingly be effected by partial separation of the benzene.

The invention claimed is:

1. A process for continuously producing nitrobenzene comprising
   a) nitrating benzene with a mixture of nitric acid and sulfuric acid under adiabatic conditions to obtain a product;
   b) separating the product obtained in step a) by phase separation into an aqueous phase comprising sulfuric acid, nitrobenzene, and benzene, and an organic phase comprising nitrobenzene and benzene;
   c) transferring the aqueous phase obtained in step b) into an evaporator wherein the sulfuric acid is concentrated by pressure reduction, wherein a gaseous stream comprising water, nitrobenzene, and benzene is removed from the evaporator and then condensed, and wherein the resulting concentrated sulfuric acid is fed back into step a);
   d) separating via distillation from 20% by mass to 100% by mass of the benzene contained in the organic phase obtained in step b) by evaporating the benzene using the adiabatic heat of reaction obtained in step a), wherein a pre-purified nitrobenzene depleted of benzene is obtained;

e) washing the pre-purified nitrobenzene obtained in step d) with at least one aqueous phase and subsequently separating the at least one aqueous phase from the nitrobenzene by phase separation to obtain purified nitrobenzene.

2. The process of claim 1, wherein in step d) from 20% by mass to 99.8% by mass of the benzene contained in the organic phase obtained in step b) is separated off and step e) is followed by:

f) separating via distillation benzene and water from the purified nitrobenzene obtained in step e) to obtain dried pure nitrobenzene.

3. The process of claim 1, further comprising removing the water from the condensed gaseous stream obtained in step c) and then feeding the resulting stream comprising benzene and nitrobenzene to the distillation of step d).

4. The process of claim 1, wherein the at least one aqueous phase in step e) is selected from the group consisting of an acid aqueous phase, an alkaline aqueous phase, and a neutral aqueous phase.

5. The process of claim 1, wherein from greater than 99.8% by mass to 100% by mass of the benzene contained in the organic phase obtained in step b) is separated off.

6. The process of claim 5, wherein the purified nitrobenzene obtained in step e) is not purified further.

7. The process of claim 2, wherein the dried pure nitrobenzene obtained in step f) is not purified further.

8. A process comprising hydrogenating the purified nitrobenzene obtained in claim 6 to obtain aniline.

9. A process comprising hydrogenating the dried pure nitrobenzene obtained in claim 7 to obtain aniline.

* * * * *